(12) United States Patent
Mansfield

(10) Patent No.: US 11,529,532 B2
(45) Date of Patent: *Dec. 20, 2022

(54) RADIATION THERAPY SYSTEMS AND METHODS

(71) Applicant: Varian Medical Systems, Inc., Palo Alto, CA (US)

(72) Inventor: Stanley Mansfield, Sunnyvale, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/182,031

(22) Filed: Feb. 22, 2021

(65) Prior Publication Data

US 2021/0170202 A1 Jun. 10, 2021

Related U.S. Application Data

(63) Continuation of application No. 16/401,387, filed on May 2, 2019, now Pat. No. 10,960,231, which is a (Continued)

(51) Int. Cl.
*A61N 5/10* (2006.01)

(52) U.S. Cl.
CPC ......... *A61N 5/1077* (2013.01); *A61N 5/1043* (2013.01); *A61N 5/1049* (2013.01);
(Continued)

(58) Field of Classification Search
CPC .. A61N 5/1077; A61N 5/1043; A61N 5/1049; A61N 5/1067; A61N 2005/1087; A61N 2005/1095
See application file for complete search history.

(56) References Cited

U.S. PATENT DOCUMENTS

| 4,163,901 A | 8/1979 | Azam |
| 4,914,681 A | 4/1990 | Klingenbeck et al. |

(Continued)

FOREIGN PATENT DOCUMENTS

| CN | 104001270 | 8/2014 |
| CN | 106730407 | 5/2017 |

(Continued)

OTHER PUBLICATIONS

M. McManus et al., "The challenge of ionisation chamber dosimetry in ultra-short pulsed high dose-rate Very High Energy Electron beams," Sci Rep 10, 9089 (2020), published Jun. 3, 2020, https://doi.org/10.1038/S41598-020-65819-y.

(Continued)

*Primary Examiner* — David A Vanore

(57) ABSTRACT

A radiation therapy system includes an accelerator and beam transport system that generates a beam of particles. The accelerator and beam transport system guides the beam on a path and into a nozzle that is operable for aiming the beam toward an object. The nozzle includes a scanning magnet operable for steering the beam toward different locations within the object, and also includes a beam energy adjuster configured to adjust the beam by, for example, placing different thicknesses of material in the path of the beam to affect the energies of the particles in the beam.

18 Claims, 7 Drawing Sheets

US 11,529,532 B2

Page 2

Related U.S. Application Data continuation of application No. 15/850,472, filed on Dec. 21, 2017, now Pat. No. 10,307,618, which is a continuation of application No. 15/089,330, filed on Apr. 1, 2016, now Pat. No. 9,855,445.

(52) U.S. Cl.
CPC .... *A61N 5/1067* (2013.01); *A61N 2005/1087* (2013.01); *A61N 2005/1095* (2013.01)

(56) References Cited

U.S. PATENT DOCUMENTS

| | | |
|---|---|---|
| 5,153,900 A | 10/1992 | Nomikos et al. |
| 5,267,294 A | 11/1993 | Kuroda |
| 5,550,378 A | 8/1996 | Skillicorn et al. |
| 5,610,967 A | 3/1997 | Moorman et al. |
| 5,625,663 A | 4/1997 | Swerdloff et al. |
| 5,682,412 A | 10/1997 | Skillicorn et al. |
| 5,757,885 A | 5/1998 | Yao et al. |
| 6,198,802 B1 | 3/2001 | Elliott et al. |
| 6,222,544 B1 | 4/2001 | Tarr et al. |
| 6,234,671 B1 | 5/2001 | Solomon et al. |
| 6,260,005 B1 | 7/2001 | Yang et al. |
| 6,328,395 B1* | 12/2001 | Kitahara ............. B41J 2/04541 347/15 |
| 6,379,380 B1 | 4/2002 | Satz |
| 6,411,675 B1 | 6/2002 | Llacer |
| 6,445,766 B1 | 9/2002 | Whitham |
| 6,504,899 B2 | 1/2003 | Pugachev et al. |
| 6,580,940 B2 | 6/2003 | Gutman |
| 6,777,700 B2 | 8/2004 | Yanagisawa et al. |
| 6,993,112 B2 | 1/2006 | Hesse |
| 7,268,358 B2 | 9/2007 | Ma et al. |
| 7,385,203 B2 | 6/2008 | Nakayama et al. |
| 7,453,983 B2 | 11/2008 | Schildkraut et al. |
| 7,515,681 B2 | 4/2009 | Ebstein |
| 7,522,706 B2 | 4/2009 | Lu et al. |
| 7,560,715 B2 | 7/2009 | Pedroni |
| 7,590,219 B2 | 9/2009 | Maurer, Jr. et al. |
| 7,616,735 B2 | 11/2009 | Maciunas et al. |
| 7,623,623 B2 | 11/2009 | Raanes et al. |
| 7,778,691 B2 | 8/2010 | Zhang et al. |
| 7,807,982 B2 | 10/2010 | Nishiuchi et al. |
| 7,831,289 B2 | 11/2010 | Riker et al. |
| 7,835,492 B1 | 11/2010 | Sahadevan |
| 7,907,699 B2 | 3/2011 | Long et al. |
| 8,284,898 B2 | 10/2012 | Ho et al. |
| 8,306,184 B2 | 11/2012 | Chang et al. |
| 8,401,148 B2 | 3/2013 | Lu et al. |
| 8,406,844 B2 | 3/2013 | Ruchala et al. |
| 8,559,596 B2 | 10/2013 | Thomson et al. |
| 8,600,003 B2 | 12/2013 | Zhou et al. |
| 8,613,694 B2 | 12/2013 | Walsh |
| 8,636,636 B2 | 1/2014 | Shukla et al. |
| 8,644,571 B1 | 2/2014 | Schulte et al. |
| 8,716,663 B2 | 5/2014 | Brusasco et al. |
| 8,836,332 B2 | 9/2014 | Shvartsman et al. |
| 8,847,179 B2 | 9/2014 | Fujitaka et al. |
| 8,903,471 B2 | 12/2014 | Heid |
| 8,917,813 B2 | 12/2014 | Maurer, Jr. |
| 8,948,341 B2 | 2/2015 | Beckman |
| 8,958,864 B2 | 2/2015 | Amies et al. |
| 8,983,573 B2 | 3/2015 | Carlone et al. |
| 8,986,186 B2 | 3/2015 | Zhang et al. |
| 8,992,404 B2 | 3/2015 | Graf et al. |
| 8,995,608 B2 | 3/2015 | Zhou et al. |
| 9,018,603 B2 | 4/2015 | Loo et al. |
| 9,033,859 B2 | 5/2015 | Fieres et al. |
| 9,079,027 B2 | 7/2015 | Agano et al. |
| 9,149,656 B2 | 10/2015 | Tanabe |
| 9,155,908 B2 | 10/2015 | Meltsner et al. |
| 9,233,260 B2 | 1/2016 | Slatkin et al. |
| 9,258,876 B2 | 2/2016 | Cheung et al. |
| 9,283,406 B2 | 3/2016 | Prieels |
| 9,308,391 B2 | 4/2016 | Liu et al. |
| 9,330,879 B2 | 5/2016 | Lewellen et al. |
| 9,333,374 B2 | 5/2016 | Iwata |
| 9,468,777 B2 | 10/2016 | Fallone et al. |
| 9,517,358 B2 | 12/2016 | Velthuis et al. |
| 9,526,918 B2 | 12/2016 | Kruip |
| 9,545,444 B2 | 1/2017 | Strober et al. |
| 9,583,302 B2 | 2/2017 | Figueroa Saavedra et al. |
| 9,636,381 B2 | 5/2017 | Basile |
| 9,636,525 B1 | 5/2017 | Sahadevan |
| 9,649,298 B2 | 5/2017 | Djonov et al. |
| 9,656,098 B2 | 5/2017 | Goer |
| 9,694,204 B2 | 7/2017 | Hardemark |
| 9,776,017 B2 | 10/2017 | Flynn et al. |
| 9,786,054 B2 | 10/2017 | Taguchi et al. |
| 9,786,093 B2 | 10/2017 | Svensson |
| 9,786,465 B2 | 10/2017 | Li et al. |
| 9,795,806 B2 | 10/2017 | Matsuzaki et al. |
| 9,801,594 B2 | 10/2017 | Boyd et al. |
| 9,844,358 B2 | 12/2017 | Wiggers et al. |
| 9,854,662 B2 | 12/2017 | Mishin |
| 9,855,445 B2* | 1/2018 | Mansfield ............ A61N 5/1067 |
| 9,884,206 B2 | 2/2018 | Schulte et al. |
| 9,931,522 B2 | 4/2018 | Bharadwaj et al. |
| 9,962,562 B2 | 5/2018 | Fahrig et al. |
| 9,974,977 B2 | 5/2018 | Lachaine et al. |
| 9,987,502 B1 | 6/2018 | Gattiker et al. |
| 10,007,961 B2 | 6/2018 | Grudzinski et al. |
| 10,022,564 B2 | 7/2018 | Thieme et al. |
| 10,071,264 B2 | 9/2018 | Liger |
| 10,080,912 B2 | 9/2018 | Kwak et al. |
| 10,092,774 B1* | 10/2018 | Vanderstraten ........ G16H 50/50 |
| 10,183,179 B1* | 1/2019 | Smith .................. A61N 5/1067 |
| 10,188,875 B2 | 1/2019 | Kwak et al. |
| 10,206,871 B2 | 2/2019 | Lin et al. |
| 10,212,800 B2 | 2/2019 | Agustsson et al. |
| 10,232,193 B2 | 3/2019 | Iseki |
| 10,258,810 B2 | 4/2019 | Zwart et al. |
| 10,272,264 B2 | 4/2019 | Ollila et al. |
| 10,279,196 B2 | 5/2019 | West et al. |
| 10,293,184 B2 | 5/2019 | Pishdad et al. |
| 10,307,614 B2 | 6/2019 | Schnarr |
| 10,307,615 B2 | 6/2019 | Ollila et al. |
| 10,307,618 B2* | 6/2019 | Mansfield ............ A61N 5/1049 |
| 10,315,047 B2 | 6/2019 | Glimelius et al. |
| 10,413,755 B1 | 9/2019 | Sahadevan |
| 10,449,389 B2 | 10/2019 | Ollila et al. |
| 10,485,988 B2 | 11/2019 | Kuusela et al. |
| 10,525,285 B1 | 1/2020 | Friedman |
| 10,549,117 B2 | 2/2020 | Vanderstraten et al. |
| 10,603,514 B2 | 3/2020 | Grittani et al. |
| 10,609,806 B2* | 3/2020 | Roecken ............. A61N 5/1043 |
| 10,636,609 B1 | 4/2020 | Bertsche et al. |
| 10,646,728 B2* | 5/2020 | Zwart .................. A61N 5/1043 |
| 10,660,588 B2 | 5/2020 | Boyd et al. |
| 10,661,100 B2 | 5/2020 | Shen |
| 10,682,528 B2 | 6/2020 | Ansorge et al. |
| 10,702,716 B2* | 7/2020 | Heese .................. A61N 5/1071 |
| 10,758,746 B2 | 9/2020 | Kwak et al. |
| 10,870,018 B2 | 12/2020 | Bartkoski et al. |
| 10,960,231 B2* | 3/2021 | Mansfield ............ A61N 5/1043 |
| 2004/0104354 A1 | 6/2004 | Haberer et al. |
| 2006/0226372 A1 | 10/2006 | Yanagisawa et al. |
| 2007/0287878 A1 | 12/2007 | Fantini et al. |
| 2008/0023644 A1 | 1/2008 | Pedroni |
| 2009/0063110 A1 | 3/2009 | Failla et al. |
| 2009/0287467 A1 | 11/2009 | Sparks et al. |
| 2010/0119032 A1 | 5/2010 | Yan et al. |
| 2010/0177870 A1 | 7/2010 | Nord et al. |
| 2010/0178245 A1 | 7/2010 | Arnsdorf et al. |
| 2010/0260317 A1 | 10/2010 | Chang et al. |
| 2011/0006224 A1 | 1/2011 | Maltz et al. |
| 2011/0091015 A1 | 4/2011 | Yu et al. |
| 2011/0135058 A1 | 6/2011 | Sgouros et al. |
| 2011/0240874 A1 | 10/2011 | Iwata |
| 2012/0076271 A1 | 3/2012 | Yan et al. |
| 2012/0157746 A1 | 6/2012 | Meltsner et al. |
| 2012/0171745 A1 | 7/2012 | Itoh |
| 2012/0197058 A1 | 8/2012 | Shukla et al. |

(56) References Cited

U.S. PATENT DOCUMENTS

| | | |
|---|---|---|
| 2013/0116929 A1 | 5/2013 | Carlton et al. |
| 2013/0150922 A1 | 6/2013 | Butson et al. |
| 2013/0177641 A1 | 7/2013 | Ghoroghchian |
| 2013/0231516 A1 | 9/2013 | Loo et al. |
| 2014/0091734 A1 | 4/2014 | Gall et al. |
| 2014/0177807 A1 | 6/2014 | Lewellen et al. |
| 2014/0185776 A1 | 7/2014 | Li et al. |
| 2014/0206926 A1 | 7/2014 | van der Laarse |
| 2014/0275706 A1 | 9/2014 | Dean et al. |
| 2014/0369476 A1 | 12/2014 | Harding |
| 2015/0011817 A1 | 1/2015 | Feng |
| 2015/0202464 A1 | 7/2015 | Brand et al. |
| 2015/0306423 A1 | 10/2015 | Bharat et al. |
| 2016/0279444 A1 | 9/2016 | Schlosser |
| 2016/0310764 A1 | 10/2016 | Bharadwaj et al. |
| 2017/0128746 A1* | 5/2017 | Zwart ............ A61N 5/1077 |
| 2017/0157422 A1* | 6/2017 | Zwart ............ A61N 5/1043 |
| 2017/0189721 A1 | 7/2017 | Sumanaweera et al. |
| 2017/0203129 A1 | 7/2017 | Dessy |
| 2017/0281973 A1 | 10/2017 | Allen et al. |
| 2017/0281981 A1* | 10/2017 | Mansfield ........ A61N 5/1067 |
| 2018/0021594 A1 | 1/2018 | Papp et al. |
| 2018/0043183 A1 | 2/2018 | Sheng et al. |
| 2018/0056090 A1 | 3/2018 | Jordan et al. |
| 2018/0099154 A1 | 4/2018 | Prieels |
| 2018/0099155 A1 | 4/2018 | Prieels et al. |
| 2018/0099159 A1 | 4/2018 | Forton et al. |
| 2018/0133514 A1* | 5/2018 | Mansfield ........ A61N 5/1043 |
| 2018/0154183 A1 | 6/2018 | Sahadevan |
| 2018/0197303 A1 | 7/2018 | Jordan et al. |
| 2018/0207425 A1 | 7/2018 | Carlton et al. |
| 2018/0236268 A1 | 8/2018 | Zwart et al. |
| 2019/0022407 A1* | 1/2019 | Abel .................. B33Y 50/02 |
| 2019/0022422 A1* | 1/2019 | Trail .................. H01J 35/14 |
| 2019/0054315 A1 | 2/2019 | Isola et al. |
| 2019/0070435 A1 | 3/2019 | Joe Anto et al. |
| 2019/0168027 A1* | 6/2019 | Smith ............ A61N 5/1067 |
| 2019/0255361 A1* | 8/2019 | Mansfield ........ A61N 5/1067 |
| 2019/0299027 A1 | 10/2019 | Fujii et al. |
| 2019/0299029 A1 | 10/2019 | Inoue |
| 2019/0351259 A1 | 11/2019 | Lee et al. |
| 2020/0001118 A1 | 1/2020 | Snider, III et al. |
| 2020/0022248 A1 | 1/2020 | Yi et al. |
| 2020/0030633 A1 | 1/2020 | Van Heteren et al. |
| 2020/0035438 A1* | 1/2020 | Star-Lack ............ H01J 35/08 |
| 2020/0069818 A1 | 3/2020 | Jaskula-Ranga et al. |
| 2020/0164224 A1 | 5/2020 | Vanderstraten et al. |
| 2020/0178890 A1 | 6/2020 | Otto |
| 2020/0197730 A1 | 6/2020 | Safavi-Naeini et al. |
| 2020/0254279 A1 | 8/2020 | Ohishi |
| 2020/0269068 A1* | 8/2020 | Abel ................ A61N 5/1045 |
| 2020/0276456 A1 | 9/2020 | Swerdloff |
| 2020/0282234 A1 | 9/2020 | Folkerts et al. |
| 2021/0170202 A1* | 6/2021 | Mansfield ........ A61N 5/1077 |

FOREIGN PATENT DOCUMENTS

| | | |
|---|---|---|
| CN | 107362464 | 11/2017 |
| CN | 109966662 | 7/2019 |
| CN | 111481840 | 8/2020 |
| CN | 111481841 | 8/2020 |
| EA | 010207 | 6/2008 |
| EP | 0979656 | 2/2000 |
| EP | 3338858 | 6/2018 |
| EP | 3384961 | 10/2018 |
| EP | 3421087 | 1/2019 |
| EP | 3453427 | 3/2019 |
| EP | 3586920 | 1/2020 |
| JP | 2617283 | 6/1997 |
| JP | 2019097969 | 6/2019 |
| WO | 2007017177 | 2/2007 |
| WO | 2010018476 | 2/2010 |
| WO | 2013081218 | 6/2013 |
| WO | 2013133936 | 9/2013 |
| WO | 2014139493 | 9/2014 |
| WO | 2015038832 | 3/2015 |
| WO | 2015102680 | 7/2015 |
| WO | 2016122957 | 8/2016 |
| WO | 2017156316 | 9/2017 |
| WO | 2017174643 | 10/2017 |
| WO | 2018137772 | 8/2018 |
| WO | 2018152302 | 8/2018 |
| WO | 2019097250 | 5/2019 |
| WO | 2019103983 | 5/2019 |
| WO | 2019164835 | 8/2019 |
| WO | 2019166702 | 9/2019 |
| WO | 2019185378 | 10/2019 |
| WO | 2019222436 | 11/2019 |
| WO | 2020018904 | 1/2020 |
| WO | 2020064832 | 4/2020 |
| WO | 2020107121 | 6/2020 |
| WO | 2020159360 | 8/2020 |

OTHER PUBLICATIONS

Ibrahim Oraiqat et al., "An Ionizing Radiation Acoustic Imaging (iRAI) Technique for Real-Time Dosimetric Measurements for FLASH Radiotherapy," Medical Physics, vol. 47, Issue10, Oct. 2020, pp. 5090-5101, First published: Jun. 27, 2020, https://doi.org/10.1002/mp.14358.

K. Petersson et al., "Dosimetry of ultra high dose rate irradiation for studies on the biological effect induced in normal brain and GBM," ICTR-PHE 2016, p. S84, Feb. 2016, https://publisher-connector.core.ac.uk/resourcesync/data/elsevier/pdf/14c/aHR0cDovL2FwaS5lbHNldmllci5jb20vY29udGVudC9hcnRpY2xlL3BpaS9zMDE2NzgxNDAxNjMwMTcyNA==.pdf.

Susanne Auer et al., "Survival of tumor cells after proton irradiation with ultra-high dose rates," Radiation Oncology 2011, 6:139, Published Oct. 18, 2011, DOI: https://doi.org/10.1186/1748-717X-6-139.

Cynthia E. Keen, "Clinical linear accelerator delivers FLASH radiotherapy," Physics World, Apr. 23, 2019, IOP Publishing Ltd, https://physicsworld.com/a/clinical-linear-accelerator-delivers-flash-radiotherapy/.

Fan et al., "Emission guided radiation therapy for lung and prostate cancers: A feasibility study on a digital patient," Med Phys. Nov. 2012; 39(11): 7140-7152. Published online Nov. 5, 2012. https://www.ncbi.nlm.nih.gov/pmc/articles/PMC3505203/doi: 10.1118/1.4761951.

Favaudon et al., "Ultrahigh dose-rate, "flash" irradiation minimizes the side-effects of radiotherapy," Cancer / Radiotherapy, vol. 19, Issues 6-7, Oct. 2015, pp. 526-531, Available online Aug. 12, 2015, https://doi.org/10.1016/j.canrad.2015.04.006.

O. Zlobinskaya et al., "The Effects of Ultra-High Dose Rate Proton Irradiation on Growth Delay in the Treatment of Human Tumor Xenografts in Nude Mice," Radiation Research, 181(2):177-183. Published Feb. 13, 2014, DOI: http://dx.doi.org/10.1667/RR13464.1.

Bjorn Zackrisson, "Biological Effects of High Energy Radiation and Ultra High Dose Rates," Umea University Medical Dissertations, New series No. 315—ISSN 0346-6612, From the Department of Oncology, University of Umea, Umea, Sweden, ISBN 91-7174-614-5, Printed in Sweden by the Printing Office of Umea University, Umea, 1991.

P. Montay-Gruel et al., "Irradiation in a flash: Unique sparing of memory in mice after whole brain irradiation with dose rates above 100 Gy/s," Radiotherapy and Oncology, vol. 124, Issue 3, Sep. 2017, pp. 365-369, Available online May 22, 2017, doi: 10.1016/j.radonc.2017.05.003.

BW Loo et al., "Delivery of Ultra-Rapid Flash Radiation Therapy and Demonstration of Normal Tissue Sparing After Abdominal Irradiation of Mice," International Journal of Radiation Oncology, Biology, Physics, vol. 98, Issue 2, p. E16, Supplement: S Meeting Abstract: P003, Published: Jun. 1, 2017, DOI: https://doi.org/10.1016/j.ijrobp.2017.02.101.

Bhanu Prasad Venkatesulu et al., "Ultra high dose rate (35 Gy/sec) radiation does not spare the normal tissue in cardiac and splenic

(56) References Cited

OTHER PUBLICATIONS models of lymphopenia and gastrointestinal syndrome," Sci Rep 9, 17180 (2019), Published Nov. 20, 2019, DOI: https://doi.org/10.1038/s41598-019-53562-y.
P. Montay-Gruel et al., "Long-term neurocognitive benefits of FLASH radiotherapy driven by reduced reactive oxygen species," PNAS May 28, 2019, vol. 116, No. 22, pp. 10943-10951; first published May 16, 2019, https://doi.org/10.1073/pnas.1901777116.
Peter G. Maxim et al., "FLASH radiotherapy: Newsflash or flash in the pan?", Medical Physics, 46 (10), Oct. 2019, pp. 4287-4290, American Association of Physicists in Medicine, First published: Jun. 27, 2019, https://doi.org/10.1002/mp.13685.
Andrei Pugachev et al., "Pseudo beam's-eye-view as applied to beam orientation selection in intensity-modulated radiation therapy," Int. J. Radiation Oncology Biol. Phys., vol. 51, Issue 5, p. 1361-1370, Dec. 1, 2001, DOI: https://doi.org/10.1016/S0360-3016(01)01736-9.
Xiaodong Zhang et al., "Intensity-Modulated Proton Therapy Reduces the Dose to Normal Tissue Compared With Intensity-Modulated Radiation Therapy or Passive Scattering Proton Therapy and Enables Individualized Radical Radiotherapy for Extensive Stage IIIB Non-Small-Cell Lung Cancer: A Virtual Clinical Study," Int. J. Radiation Oncology Biol. Phys., vol. 77, No. 2, pp. 357-366, 2010, Available online Aug. 5, 2009, DOI: https://doi.org/10.1016/j.ijrobp.2009.04.028.
A. J. Lomax et al., "Intensity modulated proton therapy: A clinical example," Medical Physics, vol. 28, Issue 3, Mar. 2001, pp. 317-324, First published: Mar. 9, 2001, https://doi.org/10.1118/1.1350587.
Lamberto Widesott et al., "Intensity-Modulated Proton Therapy Versus Helical Tomotherapy in Nasopharynx Cancer: Planning Comparison and NTCP Evaluation," Int. J. Radiation Oncology Biol. Phys., vol. 72, No. 2, pp. 589-596, Oct. 1, 2008, Available online Sep. 13, 2008, DOI: https://doi.org/10.1016/j.ijrobp.2008.05.065.
Andrei Pugachev et al., "Role of beam orientation optimization in intensity-modulated radiation therapy," Int. J. Radiation Oncology Biol. Phys., vol. 50, No. 2, pp. 551-560, Jun. 1, 2001, Available online May 10, 2001, DOI: https://doi.org/10.1016/S0360-3016(01)01502-4.
Damien C. Weber et al., "Radiation therapy planning with photons and protons for early and advanced breast cancer: an overview," Radiat Oncol. 2006; 1: 22. Published online Jul. 20, 2006, doi: 10.1186/1748-717X-1-22.
RaySearch Laboratories, "Leading the way in cancer treatment, Annual Repod 2013," RaySearch Laboratories (publ), Stockholm, Sweden, 94 pages, Apr. 2014, https://www.raysearchlabs.com/siteassets/about-overview/media-center/wp-re-ev-n-pdfs/brochures/raysearch-ar-2013-eng-pdf.
Fredrik Carlsson, "Utilizing Problem Structure in Optimization of Radiation Therapy," KTH Engineering Sciences, Doctoral Thesis, Stockholm, Sweden, Apr. 2008, Optimization and Systems Theory, Department of Mathematics, Royal Institute of Technology, Stockholm, Sweden, ISSN 1401-2294, https://www.raysearchlabs.com/globalassets/about-overview/media-center/wp-re-ev-n-pdfs/publications/thesis-fredrik_light.pdf.
Chang-Ming Charlie Ma, "Physics and Dosimetric Principles of SRS and SBRT," Mathews J Cancer Sci. 4(2): 22, 2019, published: Dec. 11, 2019, ISSN: 2474-6797, DOI: https://doi.org/10.30654/MJCS.10022.
Alterego-Admin, "Conventional Radiation Therapy May Not Protect Healthy Brain Cells," International Neuropsychiatric Association— INA, Oct. 10, 2019, https://inawebsite.org/conventional-radiation-therapy-may-not-protect-healthy-brain-cells/.
Aafke Christine Kraan, "Range verification methods in particle therapy: underlying physics and Monte Carlo modeling," Frontiers in Oncology, Jul. 7, 2015, vol. 5, Article 150, 27 pages, doi: 10.3389/fonc.2015.00150.
Wayne D. Newhauser et al., "The physics of proton therapy," Physics in Medicine & Biology, Mar. 24, 2015, 60 R155-R209, Institute of Physics and Engineering in Medicine, IOP Publishing, doi: 10.1088/0031-9155/60/8/R155.
S E McGowan et al., "Treatment planning optimisation in proton therapy," Br J Radiol, 2013, 86, 20120288, The British Institute of Radiology, 12 pages, DOI: 10.1259.bjr.20120288.
Steven Van De Water et al., "Towards FLASH proton therapy: the impact of treatment planning and machine characteristics on achievable dose rates," Acta Oncologica, Jun. 26, 2019, vol. 58, No. 10, p. 1462-1469, Taylor & Francis Group, DOI: 10.1080/0284186X.2019.1627416.
J. Groen, "FLASH optimisation in clinical IMPT treatment planning," MSc Thesis, Jul. 1, 2020, Erasmus University Medical Center, department of radiotherapy, Delft University of Technology, 72 pages.
Muhammad Ramish Ashraf et al., "Dosimetry for FLASH Radiotherapy: A Review of Tools and the Role of Radioluminescence and Cherenkov Emission," Frontiers in Oncology, Aug. 21, 2020, vol. 8, Article 328, 20 pages, doi: 10.3389/fphy.2020.00328.
Emil Schuler et al., "Experimental Platform for Ultra-high Dose Rate FLASH Irradiation of Small Animals Using a Clinical Linear Accelerator," International Journal of Radiation Oncology, Biology, Physics, vol. 97, No. 1, Sep. 2016, pp. 195-203.
Elette Engels et al., "Toward personalized synchrotron microbeam radiation therapy," Scientific Reports, 10:8833, Jun. 1, 2020, 13 pages, DOI: https://doi.org/10.1038/s41598-020-65729-z.
P-H Mackeprang et al., "Assessing dose rate distributions in VMAT plans" (Accepted Version), Accepted Version: https://boris.unibe.ch/92814/8/dose_rate_project_revised_submit.pdf Published Version: 2016, Physics in medicine and biology, 61(8), pp. 3208-3221. Institute of Physics Publishing IOP, published Mar. 29, 2016, https://boris.unibe.ch/92814/.
Xiaoying Liang et al., "Using Robust Optimization for Skin Flashing in Intensity Modulated Radiation Therapy for Breast Cancer Treatment: A Feasibility Study," Practical Radiation Oncology, vol. 10, Issue 1, p. 59-69, Published by Elsevier Inc., Oct. 15, 2019.
Alexei Trofimov et al., "Optimization of Beam Parameters and Treatment Planning for Intensity Modulated Proton Therapy," Technology in Cancer Research & Treatment, vol. 2, No. 5, Oct. 2003, p. 437-444, Adenine Press.
Vladimir Anferov, "Scan pattern optimization for uniform proton beam scanning," Medical Physics, vol. 36, Issue 8, Aug. 2009, pp. 3560-3567, First published: Jul. 2, 2009.
Ryosuke Kohno et al., "Development of Continuous Line Scanning System Prototype for Proton Beam Therapy," International Journal of Particle Therapy, Jul. 11, 2017, vol. 3, Issue 4, p. 429-438, DOI: 10.14338/IJPT-16-00017.1.
Wenbo Gu et al., "Integrated Beam Orientation and Scanning-Spot Optimization in Intensity Modulated Proton Therapy for Brain and Unilateral Head and Neck Tumors," Med Phys. Author manuscript; available in PMC Apr. 1, 2019. https://www.ncbi.nlm.nih.gov/pmc/articles/PMC5904040/Published in final edited form as: Med Phys. Apr. 2018; 45(4): 1338-1350. Published online Mar. 1, 2018. doi: 10.1002/mp.12788 Accepted manuscript online: Feb. 2, 2018.
Paul Morel et al., "Spot weight adaptation for moving target in spot scanning proton therapy," Frontiers in Oncology, May 28, 2015, vol. 5, Article 119, 7 pages, doi: 10.3389/fonc.2015.00119.
Simeon Nill et al., "Inverse planning of intensity modulated proton therapy," Zeitschrift fur Medizinische Physik, vol. 14, Issue 1, 2004, pp. 35-40, https://doi.org/10.1078/0939-3889-00198.
A. Lomax, "Intensity modulation methods for proton radiotherapy," Physics in Medicine & Biology, Jan. 1999, vol. 44, No. 1, pp. 185-205, doi: 10.1088/0031-9155/44/1/014.
M Kramer et al., "Treatment planning for heavy-ion radiotherapy: physical beam model and dose optimization," Physics in Medicine & Biology, 2000, vol. 45, No. 11, pp. 3299-3317, doi: 10.1088/0031-9155/45/11/313.
Harald Paganetti, "Proton Beam Therapy," Jan. 2017, Physics World Discovery, IOP Publishing Ltd, Bristol, UK, 34 pages, DOI: 10.1088/978-0-7503-1370-4.
Shinichi Shimizu et al., "A Proton Beam Therapy System Dedicated to Spot-Scanning Increases Accuracy with Moving Tumors by

(56) References Cited

OTHER PUBLICATIONS

Real-Time Imaging and Gating and Reduces Equipment Size," PLoS One, Apr. 18, 2014, vol. 9, Issue 4, e94971, https://doi.org/10.1371/journal.pone.0094971.
Heng Li et al., "Reducing Dose Uncertainty for Spot-Scanning Proton Beam Therapy of Moving Tumors by Optimizing the Spot Delivery Sequence," International Journal of Radiation Oncology, Biology, Physics, vol. 93, Issue 3, Nov. 1, 2015, pp. 547-556, available online Jun. 18, 2015, https://doi.org/10.1016/j.ijrobp.2015.06.019.
Ion Beam Applications SA, "Netherlands Proton Therapy Center Delivers First Clinical Flash Irradiation," Imaging Technology News, May 2, 2019, Wainscot Media, https://www.itnonline.com/content/netherlands-proton-therapy-center-delivers-first-clinical-flash-irradiation.
R. M. De Kruijff, "FLASH radiotherapy: ultra-high dose rates to spare healthy tissue," International Journal of Radiation Biology, 2020, vol. 96, No. 4, pp. 419-423, published online: Dec. 19, 2019, https://doi.org/10.1080/09553002.2020.1704912.
Mevion Medical Systems, "Focus on the Future: Flash Therapy," Press Releases, Sep. 16, 2019, https://www.mevion.com/newsroom/press-releases/focus-future-flash-therapy.
Joseph D. Wilson et al., "Ultra-High Dose Rate (FLASH) Radiotherapy: Silver Bullet or Fool's Gold?", Frontiers in Oncology, Jan. 17, 2020, vol. 9, Article 1563, 12 pages, doi: 10.3389/fonc.2019.01563.
David P. Gierga, "Is Flash Radiotherapy coming?", International Organization for Medical Physics, 2020, https://www.iomp.org/iomp-news2-flash-radiotherapy/.
Abdullah Muhammad Zakaria et al., "Ultra-High Dose-Rate, Pulsed (FLASH) Radiotherapy with Carbon Ions: Generation of Early, Transient, Highly Oxygenated Conditions in the Tumor Environment," Radiation Research, Dec. 1, 2020, vol. 194, Issue 6, pp. 587-593, Radiation Research Society, Published: Aug. 27, 2020, doi: https://doi.org/10.1667/RADE-19-00015.1.
Yusuke Demizu et al., "Carbon Ion Therapy for Early-Stage Non-Small-Cell Lung Cancer," BioMed Research International, vol. 2014, Article ID 727962, 9 pages, Hindawi Publishing Corporation, published: Sep. 11, 2014, https://doi.org/10.1155/2014/727962.
Ivana Dokic et al., "Next generation multi-scale biophysical characterization of high precision cancer particle radiotherapy using clinical proton, helium-, carbon- and oxygen ion beams," Oncotarget, Aug. 30, 2016, vol. 7, No. 35, pp. 56676-56689, published online: Aug. 1, 2016, doi: 10.18632/oncotarget.10996.
Aetna Inc., "Proton Beam, Neutron Beam, and Carbon Ion Radiotherapy," 2020, No. 0270, http://www.aetna.com/cpb/medical/data/200_299/0270.html.
Nicholas W. Colangelo et al., "The Importance and Clinical Implications of FLASH Ultra-High Dose-Rate Studies for Proton and Heavy Ion Radiotherapy," Radiat Res. Author manuscript; available in PMC Jan. 1, 2021. https://www.ncbi.nlm.nih.gov/pmc/articles/PMC6949397/Published in final edited form as: Radiat Res. Jan. 2020; 193(1): 1-4. Published online Oct. 28, 2019. doi: 10.1667/RR15537.1.
Vincent Favaudon et al., "Ultrahigh dose-rate FLASH irradiation increases the differential response between normal and tumor tissue in mice," Science Translational Medicine, Jul. 16, 2014, vol. 6, Issue 245, 245ra93, American Association for the Advancement of Science, DOI: 10.1126/scitranslmed.3008973.
"FlashRad: Ultra-high dose-rate FLASH radiotherapy to minimize the complications of radiotherapy," 2014, https://siric.curie.fr/sites/default/files/atoms/files/flashrad.pdf.
Tami Freeman, "FLASH radiotherapy: from preclinical promise to the first human treatment," Physics World, Aug. 6, 2019, IOP Publishing Ltd, https://physicsworld.com/a/flash-radiotherapy-from-preclinical-promise-to-the-first-human-treatment/.
IntraOp Medical, Inc., "IntraOp and Lausanne University Hospital Announce Collaboration in FLASH radiotherapy," Jun. 18, 2020, https://intraop.com/news-events/lausanne-university-flash-radiotherapy-collaboration/.

M.-C. Vozenin et al., "Biological Benefits of Ultra-high Dose Rate FLASH Radiotherapy: Sleeping Beauty Awoken," Clin Oncol (R Coll Radiol). Author manuscript; available in PMC Nov. 12, 2019. https://www.ncbi.nlm.nih.gov/pmc/articles/PMC6850216/ Published in final edited form as: Clin Oncol (R Coll Radiol). Jul. 2019; 31(7): 407-415. Published online Apr. 19, 2019. doi: 10.1016/j.clon.2019 04.001.
Efstathios Kamperis et al., "A FLASH back to radiotherapy's past and then fast forward to the future," J Cancer Prev Curr Res. 2019;10(6):142-144. published Nov. 13, 2019, DOI: 10.15406/jcpcr.2019.10.00407.
P. Symonds et al., "FLASH Radiotherapy: The Next Technological Advance in Radiation Therapy?", Clinical Oncology, vol. 31, Issue 7, p. 405-406, Jul. 1, 2019, The Royal College of Radiologists, Published by Elsevier Ltd., DOI: https://doi.org/10.1016/j.clon.2019.05.011.
Swati Girdhani et al., "Abstract LB-280: FLASH: A novel paradigm changing tumor irradiation platform that enhances therapeutic ratio by reducing normal tissue toxicity and activating immune pathways," Proceedings: AACR Annual Meeting 2019; Mar. 29-Apr. 3, 2019; Atlanta, GA, published Jul. 2019, vol. 79, Issue 13 Supplement, pp. LB-280, American Association for Cancer Research, DOI: https://doi.org/10.1158/1538-7445.AM2019-LB-280.
Bazalova-Carter et al., "On the capabilities of conventional x-ray tubes to deliver ultra-high (FLASH) dose rates," Med. Phys. Dec. 2019; 46 (12):5690-5695, published Oct. 23, 2019, American Association of Physicists in Medicine, doi: 10.1002/mp.13858. Epub Oct. 23, 2019. PMID: 31600830.
Manuela Buonanno et al., "Biological effects in normal cells exposed to FLASH dose rate protons," Radiother Oncol. Author manuscript; available in PMC Oct. 1, 2020. https://www.ncbi.nlm.nih.gov/pmc/articles/PMC6728238/Published in final edited form as: Radiother Oncol. Oct. 2019; 139: 51-55. Published online Mar. 5, 2019. doi: 10.1016/j.radonc.2019.02 009.
N. Rama et al., "Improved Tumor Control Through T-cell Infiltration Modulated by Ultra-High Dose Rate Proton FLASH Using a Clinical Pencil Beam Scanning Proton System," International Journal of Radiation Oncology, Biology, Physics, vol. 105, Issue 1, Supplement , S164-S165, Sep. 1, 2019, Mini Oral Sessions, DOI: https://doi.org/10.1016/j.ijrobp.2019.06.187.
Inserm Press Office, "Radiotherapy 'flashes' to reduce side effects," Press Release, Jul. 16, 2014, https://presse.inserm.fr/en/radiotherapy-flashes-to-reduce-side-effects/13394/.
Eric S. Diffenderfer et al., "Design, Implementation, and in Vivo Validation of a Novel Proton FLASH Radiation Therapy System," International Journal of Radiation Oncology, Biology, Physics, vol. 106, Issue 2, Feb. 1, 2020, pp. 440-448, Available online Jan. 9, 2020, Published by Elsevier Inc., DOI: https://doi.org/10.1016/j.ijrobp.2019.10.049.
Valerie Devillaine, "Radiotherapy and Radiation Biology," Institut Curie, Apr. 21, 2017, https://institut-curie.org/page/radiotherapy-and-radiation-biology.
Imaging Technology News, "ProNova and medPhoton to Offer Next Generation Beam Delivery, Advanced Imaging for Proton Therapy," Oct. 6, 2014, Wainscot Media, Link: https://www.itnonline.com/content/pronova-and-medphoton-offer-next-generation-beam-delivery-advanced-imaging-proton-therapy.
OncoLink Team, "Radiation Therapy: Which type is right for me?", OncoLink Penn Medicine, last reviewed Mar. 3, 2020, Trustees of the University of Pennsylvania, https://www.oncolink.org/cancer-treatment/radiation/introduction-to-radiation-therapy/radiation-therapy-which-type-is-right-for-me.
Marco Durante et al., "Faster and safer? FLASH ultra-high dose rate in radiotherapy," Br J Radiol 2018; 91(1082):Jun. 28, 2017, British Institute of Radiology, Published Online: Dec. 15, 2017, https://doi.org/10.1259/bjr.20170628.
John R. Fischer, "PMB launches FLASH radiotherapy system for use in clinical trials," HealthCare Business News, Jun. 29, 2020, DOTmed.com, Inc., https://www.dotmed.com/news/story/51662.
Marie-Catherine Vozenin et al., "The advantage of FLASH radiotherapy confirmed in mini-pig and cat-cancer patients," Clinical Cancer Research, Author Manuscript Published OnlineFirst Jun. 6,

(56) References Cited

OTHER PUBLICATIONS 2018, https://clincancerres.aacrjournals.org/content/clincanres/early/2018/06/06/1078-0432.CCR-17-3375.full.pdf.

* cited by examiner

RADIATION THERAPY SYSTEMS AND METHODS

REFERENCE TO RELATED U.S. APPLICATIONS

This application is a continuation of the application with Ser. No. 16/401,387, entitled "Radiation Therapy Systems and Methods," by S. Mansfield, filed May 2, 2019, which is a continuation of the application with Ser. No. 15/850,472, now U.S. Pat. No. 10,307,618, entitled "Radiation Therapy Systems and Methods," by S. Mansfield, filed Dec. 21, 2017, which is a continuation of the application with Ser. No. 15/089,330, now U.S. Pat. No. 9,855,445, entitled "Radiation Therapy Systems and Methods," by S. Mansfield, filed Apr. 1, 2016, all of which are hereby incorporated by reference in their entirety. This application is related to the U.S. application with Ser. No. 15/087,292, entitled "Adaptive Pencil Beam Scanning," by J. Wulff, filed Mar. 31, 2016, now U.S. Pat. No. 10,912,953, and hereby incorporated by reference in its entirety.

BACKGROUND

The use of radiation therapy to treat cancer is well known. Radiation therapy (radiotherapy) involves directing a beam of high energy particles such as electrons, protons, or heavy ions into a target volume (e.g., a tumor or lesion) in a patient.

Before the patient is treated with radiation, a treatment plan specific to that patient is developed. The plan defines various aspects of the radiotherapy using simulations and optimizations based on past experiences. For example, for intensity modulated particle therapy (IMPT), the plan can specify the appropriate beam type and the appropriate beam energy. Other parts of the plan can specify, for example, the angle of the beam relative to the patient/target volume, the beam shape, and the like. In general, the purpose of the treatment plan is to deliver sufficient radiation to the target volume while minimizing the exposure of surrounding healthy tissue to radiation.

Existing IMPT dose delivery techniques utilize raster scanning that takes advantage of the well-known Bragg peak characteristic of a mono-energetic particle (e.g., proton) beam. By scanning the beam in the X and Y directions, a "layer" of dose can be "painted" within the target volume. Subsequent layers are painted in overlapping raster scan patterns using particles with a different energy that would thus stop at a different range (distance). Such scan patterns usually start at the most distal edge of the planning target volume and each subsequent layer is delivered, after a pause to change the beam energy, to a lesser range thus creating a Spread Out Bragg Peak (SOBP), until the final layer is delivered to the proximal edge of the planning target volume.

A fundamental concern during radiation therapy is that the target volume might move during dose delivery (e.g., due to the patient moving, breathing, etc.). Movement during dose delivery can inadvertently place healthy tissue in the path of the radiation intended for the target volume. Although it is theoretically possible for the raster scan pattern to track in-plane motion of the target volume, by superimposing the raster scan pattern with the instantaneous two-dimensional (X-Y) vector corresponding to that motion, any out-of-plane motions (particularly those of normal healthy structures proximal to the target) can introduce motion-related uncertainties that in turn can create dose overlaps ("hot spots") or, even worse, gaps ("cold spots") within the target volume.

A recent radiobiology study has demonstrated an advantageous effectiveness in sparing normal, healthy tissue from damage by delivering an entire, relatively high therapeutic radiation dose within a single short period of time (e.g., less than one second). However, in conventional raster-scanned IMPT, because dose delivery along each ray passing through the patient occurs successively at different points in time in the scan pattern and is thus spread out over time, the unavoidable dose that is delivered to the normal healthy structures is also spread out over time. Therefore, the radiobiological tissue-sparing effects reported in the aforementioned study are not realized using existing IMPT techniques.

Furthermore, contemporary radiation therapy delivery systems include dipole electromagnets and scanning magnets. The dipole magnets (often referred to as "bending magnets") direct (e.g., bend) the particle beam in a direction toward a nozzle, and the scanning magnets steer (deflect or scan) the beam in the X and Y directions. The dipole magnets typically utilize massive ferromagnetic return paths and therefore have a much slower magnetic hysteresis relative to the scanning magnets. That is, it takes much longer to change (increase or decrease) the level of magnetism in the dipole bending magnets than it does to steer the beam using the scanning magnets during IMPT delivery. Also, the relative slowness of varying the magnetic fields of the dipole bending magnets is the primary reason that existing IMPT systems utilize a method of scanning dose one layer at a time. The time spent changing the magnetic strength of the dipole magnets in order to change the incident beam energy constitutes a significant portion of the time required to deliver an IMPT therapy dose. Considering the comfort of the patient, for example, shorter radiotherapy sessions are highly preferred. Thus, the reliance on magnets, particularly the use of the dipole bending magnets, for adjusting particle beams is an obstacle to realizing the benefits of using relatively high therapeutic radiation doses within a very short period of time for dose delivery in radiotherapy.

SUMMARY

In an embodiment according to the present disclosure, a radiation therapy system includes an accelerator and beam transport system and a nozzle that can be aimed toward an object. The nozzle includes at least one scanning magnet that guides (e.g., steers, deflects, or scans) the beam toward various locations within a target volume within the object. The nozzle also includes a beam energy adjuster configured to adjust the beam by, for example, placing different thicknesses of material in the path of the beam to affect the energies of the particles in the beam. The beam energy adjuster may include one or both of a range shifter and a range modulator. In an embodiment, the range shifter is configured to place different thicknesses of material in the path of the beam to affect the distance that the particles penetrate into the object. In an embodiment, the range modulator is configured to place different thicknesses of material in the path of the beam to decrease the energies of at least a portion of the particles by varying the exiting beam particle energy over time, to spread out the Bragg peak.

Significantly, the range shifter and/or range modulator, placed in the nozzle as described in this disclosure, are "dynamically variable" (e.g., faster acting than the dipole magnets in the beam transport system). Consequently, a nozzle according to the present disclosure is capable of quickly adjusting the particles in the beam to create a scanned beam (as opposed to a scattered beam) that delivers an entire, relatively high therapeutic radiation dose in the target volume. For example, a dose of four grays can be delivered along a specified beam direction (e.g., a given ray) in less than one second.

Each ray is a part of a scan pattern and irradiates tissue along a different line segment through the target volume (a "target line segment"). A high dose that can be delivered in a short period of time along a target line segment may be referred to herein as a "shot." In an embodiment, a shot can be adjusted in energy (intensity) or range and delivered to the target volume with a Spread Out Bragg Peak (SOBP) that provides a uniform and otherwise suitably modified dose to an entire target line segment.

The intensity of the dose delivered in a shot can be adjusted to match the prescribed dose for a particular target line segment. Shots can be delivered using, for example, a predefined scanning pattern to irradiate different target line segments: a first adjusted beam that delivers a first dose with a SOBP along a first target line segment in a target volume can be created, and a second adjusted beam that delivers a second dose with a second SOBP along a second target line segment in the target volume can be created, where the second target line segment is displaced from the first target line segment. Each shot can be triggered in time and/or aimed in position to coincide with the position of a moving target within a patient based on, for example, a motion tracking system. Subsequent shots can be independently adjusted in intensity, in range, and with a suitable SOBP, and can also be triggered or aimed to coincide with the 4D (three dimensions plus time) position of each target line segment in the scan pattern until the entire target volume has been irradiated to the prescribed dose.

In an embodiment, a range shifter is in the nozzle, downstream of the scanning magnet(s). In another embodiment, the range shifter is in the nozzle, upstream of the scanning magnet(s). The range shifter provides a rapid means of quickly varying the range of the Bragg peak to match the distal edge of the planning target volume.

In an embodiment, the nozzle includes both a range modulator and a range shifter. The range modulator is downstream of the scanning magnet(s); the range shifter can be downstream or upstream of the scanning magnet(s). In an embodiment, the range modulator includes a number of arms extending from a hub. In an embodiment, each of the arms has a non-uniform thickness and a non-uniform width (and therefore a non-uniform amount of space between adjacent arms). The range modulator can rotate about the hub, so that the beam will pass through at least one of the arms and also can pass through the space between adjacent arms.

In an embodiment, the range modulator can be moved in a first direction (e.g., laterally, transverse to the path of the beam) so that it is either completely out of the path of the beam or is in the path of the beam. In an embodiment, the range modulator can also be moved in a second direction different from (e.g., perpendicular to) the first direction and transverse to the path of the beam.

The range modulator provides a means of quickly varying the energy in a scanned beam to create the desired extent of SOBP in a dynamically variable manner. By adjusting the position of the range modulator and rotating the range modulator, the beam can pass through different parts of at least one of its arms and therefore through different thicknesses of material and also through different amounts of space between adjacent arms, and therefore the extent of spread of the SOBP can be rapidly varied over a useful range.

The range modulator and/or the range shifter match the SOBP (distally and proximally) to the target volume (the planning target volume). Because the range modulator and the range shifter can achieve these effects quickly, a shot can advantageously be used for dose delivery. Thus, using shots, the entire target volume can be irradiated to the dose prescribed by the treatment plan while exposing healthy tissue to only a single, very short burst of radiation. Also, by delivering the entire dose within a short period of time, movement of the target volume becomes much less of an issue. Likewise, delivering a pattern of shots with varying intensity from a single beam direction quickly results in intensity-modulated radiation therapy delivery. Further, by delivering patterns of shots from multiple beam directions, a more refined intensity modulation can be achieved with lower dose delivered to healthy tissues. Importantly, because no dose is delivered distally to the Bragg peak, the dose delivered in this manner to any healthy tissue, outside the target volume, can thus be limited to a single very short burst of low dose radiation.

In summary, embodiments according to the present disclosure provide spatially and temporally precise, modulated irradiation of a moving target in a patient and take advantage of the tissue-sparing effects of the study mentioned above. Embodiments according to the present disclosure provide a more direct method for target volume scanning than the use of the conventional raster scanning technique described above. Each shot is aimed directly to coincide with the in-plane motion of the target using the scanning magnet(s), rather than having to distort the raster scan pattern. Aiming subsequent shots thusly avoids creating motion artifacts such as those caused by the interplay between the target motion of sequential raster scan patterns. Likewise, target motion in the distal-to-proximal direction can be compensated for by varying the range shifter accordingly between shots. Quality assurance is also made easier because the tracking and scanning processes are more independent of one another. Significantly, because a SOBP covering the entire length of each target line segment (from the distal edge to the proximal edge of the planning target volume) is delivered in a short burst, motion-induced uncertainties do not create gaps or overlaps (cold spots or hot spots) within the target volume.

These and other objects and advantages of the various embodiments of the present disclosure will be recognized by those of ordinary skill in the art after reading the following detailed description of the embodiments that are illustrated in the various drawing figures.

This summary is provided to introduce a selection of concepts in a simplified form that is further described below in the detailed description that follows. This summary is not intended to identify key features or essential features of the claimed subject matter, nor is it intended to be used to limit the scope of the claimed subject matter.

BRIEF DESCRIPTION OF DRAWINGS

The accompanying drawings, which are incorporated in and form a part of this specification and in which like numerals depict like elements, illustrate embodiments of the present disclosure and, together with the detailed description, serve to explain the principles of the disclosure.

DETAILED DESCRIPTION

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

A "ray" is a part of a scan pattern and irradiates tissues along a different line segment through the target volume (a "target line segment"). A high dose that can be delivered in a short period of time along a target line segment may be referred to herein as a "shot."

Figure 1:
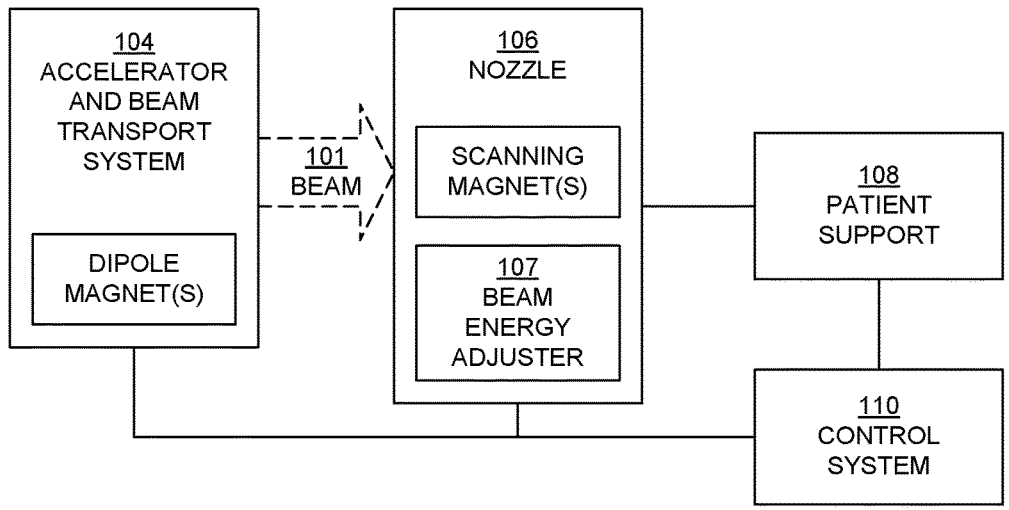
FIG. 1 is a block diagram showing selected components of a radiation therapy system upon which embodiments according to the present disclosure can be implemented.

FIG. 1 is a block diagram showing selected components of a radiation therapy system 100 upon which embodiments according to the present disclosure can be implemented. In the example of FIG. 1, the system 100 includes an accelerator and beam transport system 104 and a nozzle 106.

The accelerator and beam transport system 104 generates and accelerates a beam of charged particles, such as electrons, protons, and heavy ions, and contains the particles in a well-defined beam. In an embodiment, the accelerator is an isochronous cyclotron capable of continuous wave output. The accelerator (e.g., the cyclotron) extracts particles with a specified energy. This provides a high, continuous wave beam current for the high dose rate per shot. Other types of accelerators can be used, such as a pulsed proton accelerator such as a synchrocyclotron or a synchrotron. The accelerator (e.g., cyclotron) can be a lower power output cyclotron, such as a cyclotron that accelerates particles to the range of 70-300 MeV.

The accelerator and beam transport system 104 includes components (e.g., dipole magnets, also known as bending magnets) that direct (e.g., bend, steer, or guide) the beam through the accelerator and beam transport system in a direction toward and into the nozzle 106. The accelerator and beam transport system 104 may also include components that are used to adjust the beam energy entering the nozzle 106 so that it is different from the beam energy extracted from the accelerator. In an embodiment, sets of quadrupole magnets are located along the beam paths in the accelerator and beam transport system 104.

The nozzle 106 is used to aim the beam toward various locations within an object (e.g., a patient) supported on the supporting device 108 (e.g., a chair or table) in a treatment room. The nozzle 106 may be mounted on or a part of a gantry (not shown) so that it can be moved relative to the supporting device 108; the supporting device may also be moveable. In an embodiment, the accelerator and beam transport system 104 is also mounted on or is a part of the gantry; in another embodiment, the accelerator and beam transport system is separate from (but in communication with) the gantry.

A control system 110 receives and implements a prescribed treatment plan. In an embodiment, the control system 110 includes a computer system having a processor, memory, an input device (e.g., a keyboard), and perhaps a display in well-known fashion. The control system 110 can receive data regarding operation of the system 100. The control system 110 can control parameters of the accelerator and beam transport system 104, nozzle 106, and supporting device 108, including parameters such as the energy, intensity, direction, size, and/or shape of the beam, according to data it receives and according to the prescribed treatment plan.

As noted above, the particles entering the nozzle 106 have a specified energy. Thus, in embodiments according to the present disclosure, the nozzle 106 includes one or more components that affect (e.g., decrease, modulate) the energy of the particles in the beam. In an embodiment, the nozzle 106 also includes components (e.g., X-Y scanning magnets) that steer (e.g., guide, deflect, or scan) the beam particles in the X and Y directions, to scan a target volume in a patient on the supporting device 108.

The term "beam energy adjuster" is used herein as a general term for a component or components that affect the energy of the particles in the beam. In various embodiments, the beam energy adjuster 107 includes a range modulator, a range shifter, or both a range modulator and a range shifter. That is, when the term "beam energy adjuster" is used, then the element being discussed may be a range modulator, a range shifter, or both a range modulator and a range shifter. Note that, in an embodiment in which the beam energy adjuster includes both a range modulator and a range shifter, the range modulator and the range shifter may be separated from each other by other nozzle components. This is illustrated in further detail in FIGS. 2A, 2B, 2C, and 2D.

Figure 2A:
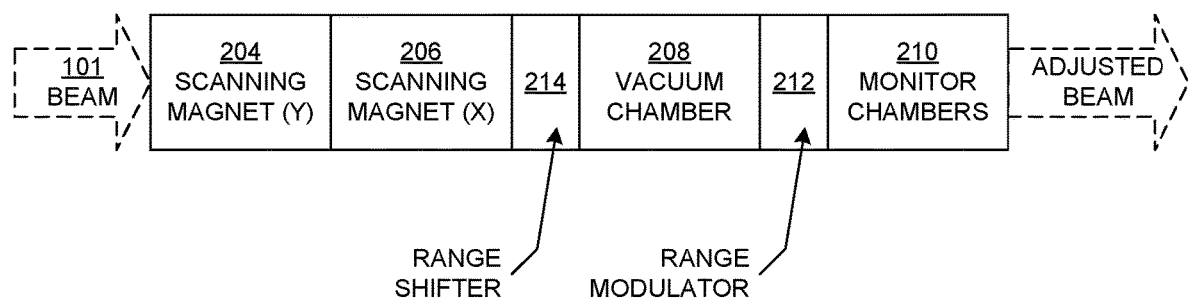
FIGS. 2A, 2B, 2C, and 2D are block diagrams illustrating selected components of a nozzle in embodiments according to the present disclosure.

FIG. 2A is a block diagram illustrating selected components of a nozzle 106A in an embodiment according to the present disclosure. The nozzle 106A receives a charged particle beam 101 from the accelerator and beam transport system 104 (FIG. 1). In the example of FIG. 2A, the nozzle 106A includes one or more scanning magnets that guide the beam 101. In an embodiment, the X-Y scanning magnets include a first (Y) magnet 204 and a second (X) magnet 206 for vertical and horizontal beam deflection to scan the beam across a planning target volume in an object (e.g., a patient). The Y-magnet 204 can be placed before or after the X-magnet 206 in the nozzle 106A.

In an embodiment, the nozzle 106A includes a vacuum chamber 208 and monitor chambers 210. The monitor chambers 210 monitor the radiation exiting from the vacuum chamber 208.

In the FIG. 2A embodiment, the nozzle 106A includes a range modulator 212 that is downstream of the X-Y scanning magnets 204 and 206. Thus, the range modulator 212 acts on a scanned particle beam (as opposed to a scattered particle beam). In an embodiment, the range modulator 212 is at the end of (outside of) the vacuum chamber, before the monitor chambers 210; the vacuum ends at the range modulator 212.

As noted above, the initial energies of the particles within the beam 101 are determined by the acceleration provided to the particles by the accelerator and beam transport system 104 (FIG. 1). The range modulator 212 varies (modulates) the energies of a portion of the particles in the scanned beam. More specifically, the range modulator 212 decreases the energy of a portion of the individual particles (e.g., by varying the exiting beam particle energy over time), thereby increasing the energy distribution of the scanned particle beam and spreading the dose distribution along the direction of travel of the scanned particle beam to deliver a dose with a Spread Out Bragg Peak (SOBP) to a target line segment (FIG. 3) in a target volume in an object (e.g., a patient).

Continuing with reference to FIG. 2A, as noted above, the range modulator 212 is located downstream of the X-Y scanning magnets 204 and 206. This avoids creating rapidly varying beam energy within the fixed or slowly varying magnetic field of the X-Y scanning magnets. This also avoids causing the beam to spread, as lower energy particles are bent more tightly than higher energy particles.

The range modulator 212 rapidly varies the exiting beam particle energy to create the desired extent of SOPB in a dynamic manner. Also, the range modulator 212 is moveable, so that it can be moved into and out of the beam path and to change the thickness of material exposed to the beam, thereby also changing the extent of the SOBP. This is further discussed below in conjunction with FIGS. 4A-4D. As will be seen by that discussion, the range modulator 212 is configured so that the extent of spread of the SOBP can be rapidly varied over a useful range in a beam that is separately being scanned in both the X and Y directions.

In the embodiment of FIG. 2A, the nozzle 106A also includes a range shifter 214. This is in contrast to a conventional radiation therapy (e.g., proton) system in which a degrader (range shifter) is located after the accelerator and before the gantry entry point. In the FIG. 2A embodiment, the range shifter 214 is in the nozzle 106A and downstream of the X-Y scanning magnets 204 and 206 and upstream of the range modulator 212. That is, the range shifter 214 is in the nozzle 106A and between the range modulator 212 and the X-Y scanning magnets 204 and 206.

The range shifter 214 is configured to change (e.g., decrease) the energies of the particles in the particle beam to affect the distance that the particles penetrate into the target volume; the range shifter affects the range of the beam. More specifically, the range shifter 214 provides a rapid means of varying the range of the Bragg peak so that the Bragg peak occurs at the distal edge of the planning target volume for each shot. An embodiment of the range shifter 214 is described further below in conjunction with FIG. 5.

In the FIG. 2A embodiment, the range modulator 212 and the range shifter 214 constitute the beam energy adjuster 107 (FIG. 1). Effectively, the range modulator 212 and the range shifter 214 each affect or adjust the beam, but in different ways: the range shifter is used for changing (e.g., decreasing) the beam energy to control the range (penetration) of the beam, and the range modulator is used for spreading out the Bragg peak.

Figure 2B:
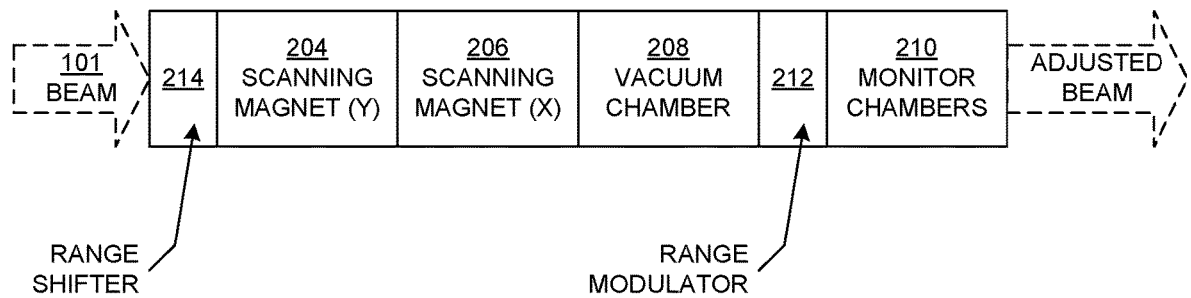

FIG. 2B is a block diagram illustrating selected components of a nozzle 106B in another embodiment according to the present disclosure. In contrast with the nozzle 106A of FIG. 2A, the range shifter 214 in the nozzle 106B is located upstream of the X-Y scanning magnets 204 and 206, between the X-Y scanning magnets and the accelerator and beam transport system 104 (FIG. 1). Locating the range shifter 214 upstream of the X-Y scanning magnets 204 and 206 means that the particle beam does not have to be compensated for the effect of the scanning magnets on the beam. In the FIG. 2B embodiment, the range modulator 212 and the range shifter 214 constitute the beam energy adjuster 107 (FIG. 1).

Figure 2C:
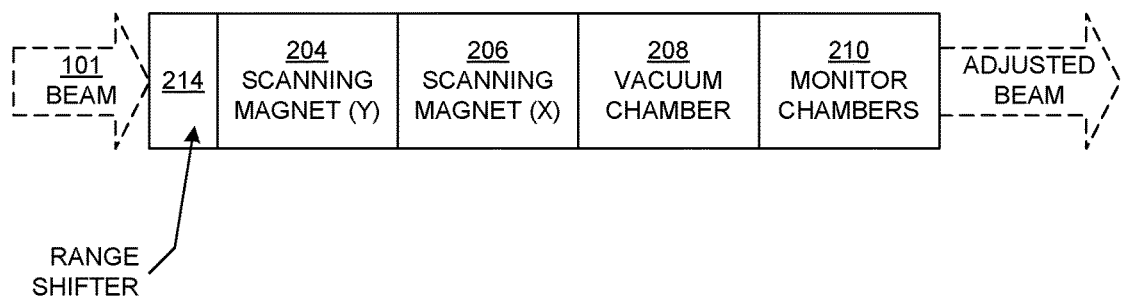

FIG. 2C is a block diagram illustrating selected components of a nozzle 106C in another embodiment according to the present disclosure. In contrast with the nozzles 106A and 106B of FIGS. 2A and 2B, respectively, the nozzle 106C includes the range shifter 214 upstream of the X-Y scanning magnets 204 and 206, between the X-Y scanning magnets and the accelerator and beam transport system 104 (FIG. 1), but does not include a range modulator. In the FIG. 2C embodiment, the range shifter 214 constitutes the beam energy adjuster 107 (FIG. 1).

Figure 2D:
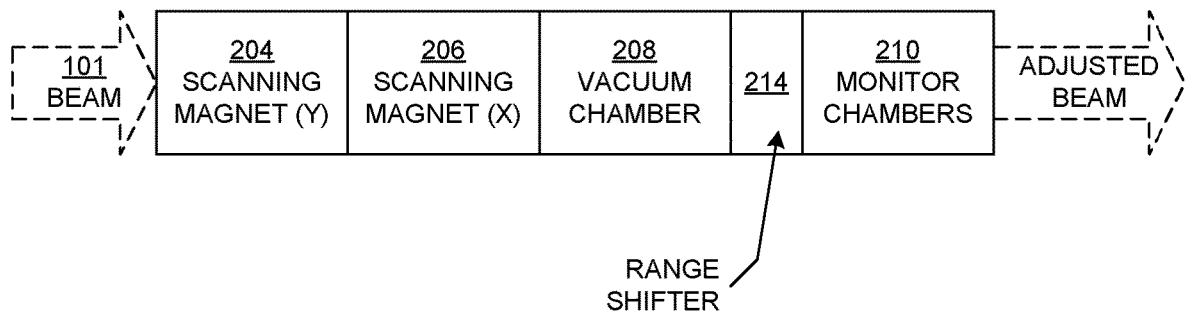

FIG. 2D is a block diagram illustrating selected components of a nozzle 106D in another embodiment according to the present disclosure. Like the nozzle 106C of FIG. 2C, the nozzle 106D includes the range shifter 214 but not a range modulator. In contrast to the FIG. 2C embodiment, the range shifter 214 is downstream of the X-Y scanning magnets 204 and 206. In the FIG. 2D embodiment, the range shifter 214 constitutes the beam energy adjuster 107 (FIG. 1).

Figure 3:
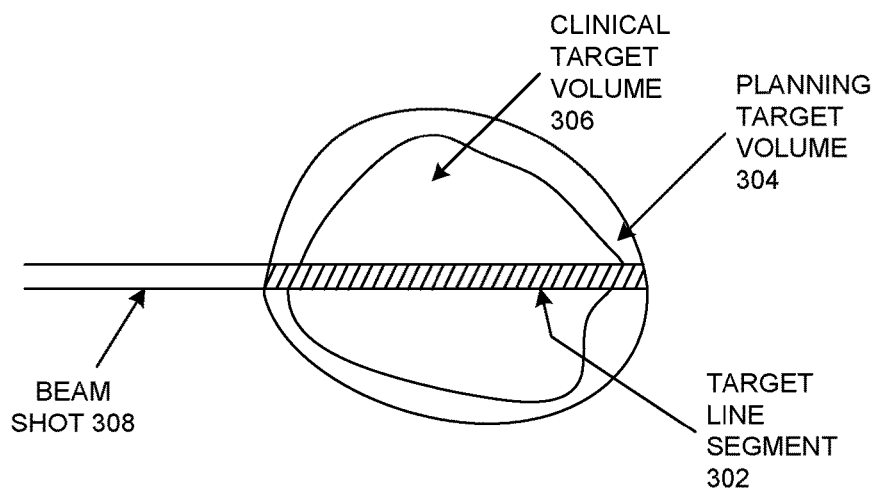
FIG. 3 illustrates an example of dose delivery along a target line segment in a planning target volume in an embodiment according to the present disclosure.

FIG. 3 illustrates an example of a target line segment 302 in a planning target volume 304. The planning target volume refers to the size of the volume to be irradiated, and encompasses the clinical target volume 306, which refers to size of the actual tumor to be treated. In the example of FIG. 3, a particle beam (shot) 308 is traveling in the direction from left to right. In the orientation of FIG. 3, the edge at the right-hand side of the planning target volume 304 (the edge furthest from the direction of the incident particle beam 308) is referred to as the distal edge, and the edge at the left-hand side of the planning target volume (the edge nearest the direction of the incident particle beam) is referred to as the proximal edge. In embodiments according to the present disclosure, the SOBP delivers a uniform dose in the direction along the target line segment 302 from the proximal edge to the distal edge.

Figure 4A:
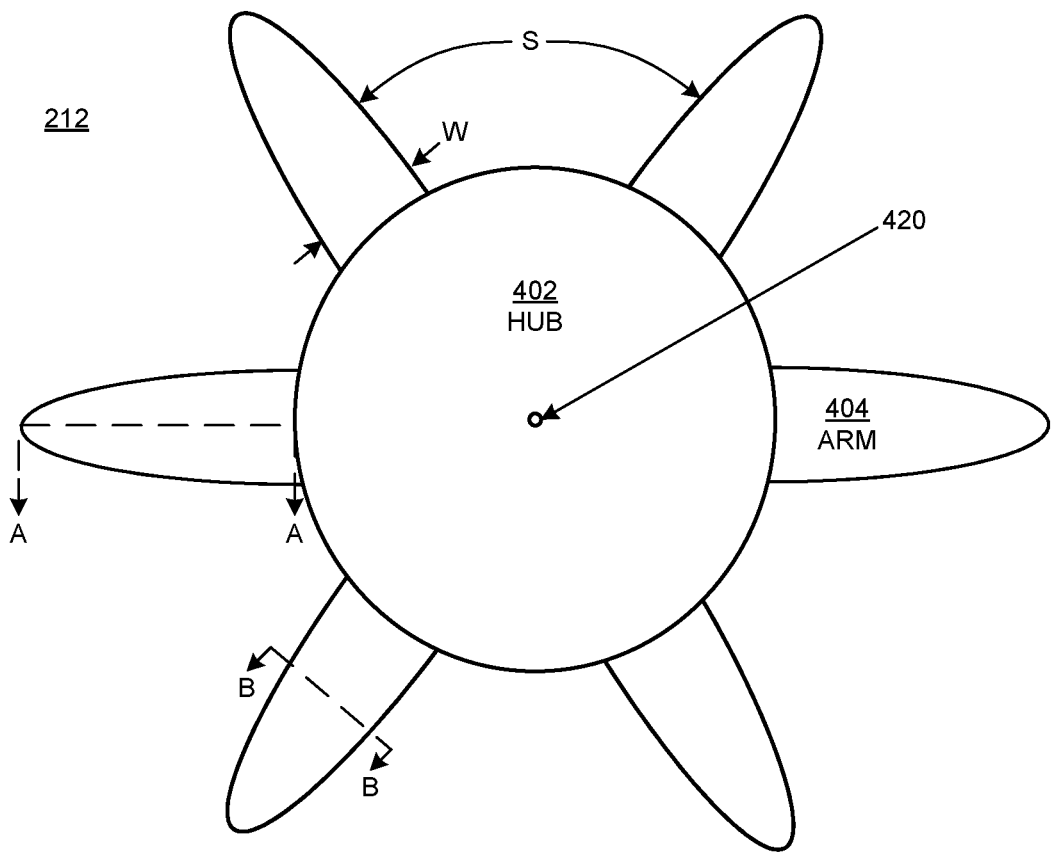
FIG. 4A illustrates a frontal view of a range modulator in an embodiment in accordance with the present disclosure.

FIG. 4A illustrates a frontal view (viewed from the perspective of the incident particle beam) of the range modulator 212 in an embodiment in accordance with the present disclosure. In this embodiment, the range modulator 212 is configured to place different thicknesses of material (including zero thickness; that is, no material) in the path of the scanned beam to vary the energy of the particles as described above. More specifically, in an embodiment, the range modulator 212 includes a number of arms 404 or blades extending from a hub 402. However, the range modulator 212 can be implemented using a single arm. In an embodiment, the arms 404 of the range modulator 212 are each made of the same material (e.g., graphite). In another embodiment, the arms 404 are made of different materials;

that is, one arm may be made of one material or combination of materials, and another arm may be made of a different material or materials.

Each of the arms 404 has a non-uniform thickness. In an embodiment, the thicknesses of the arms 404 decrease as the distance from the hub increases.

In an embodiment, the lengths of the chords of the arms 404 decrease as the distance from the hub 402 increases; that is, the widths of the arms decrease as the distance from the hub increases (where width, W, is the dimension facing the incident particle beam). Thus, in an embodiment, the amount of space, S, between the arms 404 increases as the distance from the hub 402 increases. While the arms 404 are illustrated as being semi-elliptical in shape, the present disclosure is not so limited; the arms may be more rectangular in shape, with rounded corners, for example. Generally speaking, the shapes of the arms 404 can be optimized to achieve design objectives with regard to, for example, selecting and controlling the extent of the SOBP.

The range modulator 212 can rotate clockwise and/or counter-clockwise about an axis 420 through the center of the hub 402 in order to place the arms 404 (one arm at a time) into the path of the scanned beam (into the beam line). The range modulator 212 can also rotate to a position that allows the beam to pass through the space between two adjacent arms. The range modulator 212 can rotate continuously to allow the beam to pass through a varying thickness/width of a combination of at least one arm and at least one amount of space; the varying material thickness due to that rotation creates a desired SOBP. As will be described further below, the range modulator 212 can be moved in the horizontal direction so that the incident particle beam will pass through a different part of an arm and hence through a different thickness and width of material and also through a different amount of space when the range modulator is rotated. The range modulator 212 can also be moved to a position so that it is entirely outside of the beam. In an embodiment, the range modulator 212 can also be moved in the vertical direction, allowing the range modulator to be placed virtually anywhere in or out of the beam.

Figure 4B:
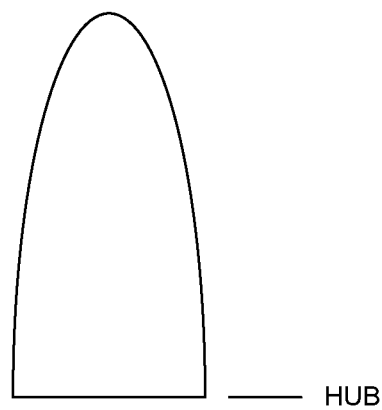
FIGS. 4B and 4C illustrate cross-sectional views of an arm of a range modulator in an embodiment according to the present disclosure.

FIG. 4B illustrates a cross-sectional view of an arm 404 along the cut-line A-A of FIG. 4A in an embodiment according to the present disclosure. In the embodiment of FIG. 4B, the thickness of the arm 404 decreases as the distance from the hub 402 increases. That is, the arm 404 is thickest where it meets the hub 402 and thinnest at its tip.

Figure 4C:
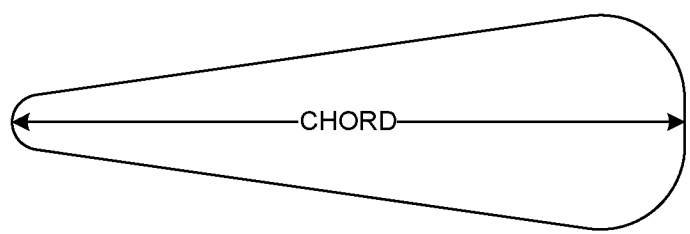

FIG. 4C illustrates a cross-sectional view of an arm 404 along the cut-line B-B of FIG. 4A in an embodiment according to the present disclosure. In the embodiment of FIG. 4C, the thickness of the arm 404 changes along its chord. That is, the arm 404 is thickest at one of its edges and thinnest at its other edge.

The shape (profile and cross-sections) of the arms 404 is not limited to the examples of FIGS. 4B and 4C.

Figure 4D:
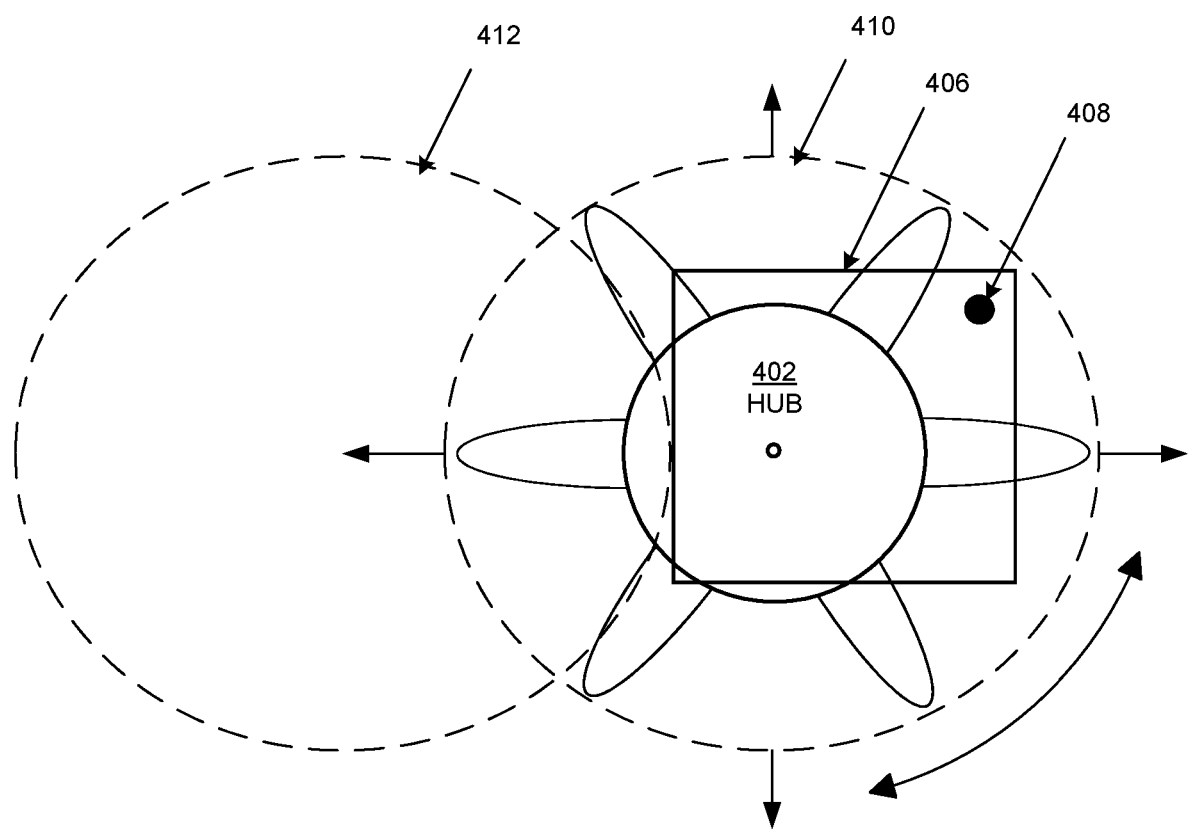
FIG. 4D illustrates positioning of a range modulator in an embodiment according to the present disclosure.

With reference to FIG. 4D, in an embodiment, the range modulator 212 can be moved in a first direction (e.g., transverse to the path of the beam) so that it is completely out of the path of the beam or is in the path of the beam. In an embodiment, the range modulator 212 can also be moved in a second direction that is different from (e.g., perpendicular to) the first direction and transverse to the path of the beam. In other words, in an embodiment, the range modulator 212 can be moved in only one direction (e.g., horizontally); and in another embodiment, the range modulator can be moved both horizontally and vertically (and hence diagonally). In an embodiment in which the range modulator 212 can move in only one direction, the diameter of the hub 402 can be sized so that it is equivalent or nearly equivalent to the maximum lateral beam scanning field width at the elevation of the hub.

Any of a number of different mechanisms can be used to move the range modulator 212 horizontally and/or vertically. For example, the range modulator 212 can be mounted on a sliding stage or assembly that allows it to be moved in either or both directions, depending on the embodiment.

In FIG. 4D, the maximum beam scanning field size is represented by a box 406, and the path of the particle beam (a beam shot) is represented by a darkened circle 408 within the box. The range modulator 212 can be positioned corresponding to the scan position of the particle beam within the maximum beam scanning field size 406, as deflected by the scanning magnets 204 and 205. For example, if the range modulator 212 is in the position indicated by the dashed circle 410, then the beam will pass through a particular thickness of one of the arms 404; if the range modulator is then moved to the right, the beam will pass through a thicker part of one of the arms; if the range modulator is instead moved to the left, the beam will pass through a thinner part of one of the arms. If the range modulator 212 is in the position indicated by the dashed circle 412, for example, then it is out of the way of any beam path. As mentioned above, the range modulator 212 can be rotating continuously while it is in position in order to create a desired SOBP; by moving the range modulator transversely (horizontally and/or vertically) to a different position, the extent of the SOBP is selected and controlled.

When the range modulator 212 is rotating in the beam path, the beam passes through at least one of the arms 404 and at least one space between adjacent arms. The speed of rotation of the range modulator 212 can be varied such that a beam shot passes through more than one arm 404 and more than one space between adjacent arms. The rotation speed of the range modulator 212 can also be adjusted so that it is synchronized with the operation of the accelerator. Any of a number of different mechanisms can be used to rotate the range modulator 212. For example, the range modulator 212 can be driven directly or indirectly by a motor connected to the hub 402.

In an embodiment, when the range modulator 212 is rotating in the beam path, the position of the range modulator in the beam path is chosen (and the range modulator is moved to that position) so that the varying material thickness due to the varying thicknesses/widths of the arms 404 and the amount of space between the arms results in the desired SOBP. At any point in time, the Bragg peak is a function of the radial distance of the beam from the hub 402. The extent of SOBP can be varied continuously from having no particle beam impingement and thus no SOBP (a pristine Bragg peak) when the beam is beyond the tip of one of the arms 404 (such as the position indicated by the dashed circle 412), to creating a maximum SOBP when the beam passes through the thickest part of one of the arms, for example, near the hub 402. The desired extent of SOBP can be achieved by moving the range modulator 212 so that the beam passes through the range modulator at a radial distance from the hub 402 corresponding to the desired SOBP. By moving the range modulator 212 rotationally and/or radially (in a horizontal and/or vertical direction), any desired SOBP can be achieved.

The range modulator 212 can be quickly positioned (rotationally and radially) and thus can be used to quickly change the SOBP, much more quickly than could be achieved using magnets. Consequently, a dose of four grays can be delivered along a target line segment in less than one second. Moreover, a dose of at least 20 grays can be delivered along a target line segment in less than 500 milliseconds.

Figure 5:
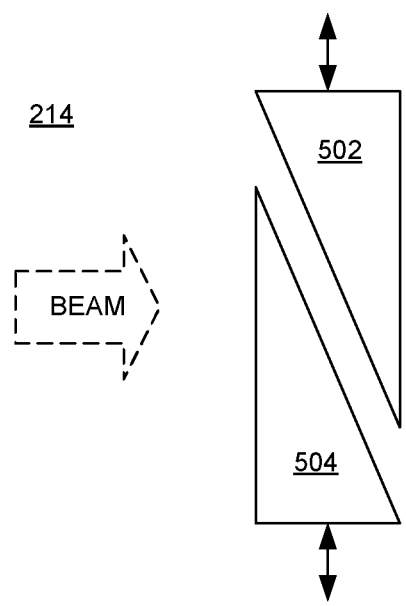
FIG. 5 illustrates a range shifter in an embodiment according to the present disclosure.

FIG. 5 illustrates a range shifter 214 in an embodiment according to the present disclosure. In this embodiment, the range shifter 214 includes a pair of wedges 502 and 504. In an embodiment, the wedges 502 and 504 are made of graphite. The wedges 502 and 504 can be moved in opposite directions to present a uniform but variable cross-sectional thickness to a particle beam passing through the wedges.

In an embodiment, the wedges 502 and 504 can be rapidly adjusted, moving along a programmed motion profile. When placed downstream of the X-Y scanning magnets 204 and 206 (FIG. 6), the wedges 502 and 504 can act as a range modulator to create a desired SOBP extent in a dynamically variable manner.

The range shifter 214 is not limited to the embodiment of FIG. 5. The range shifter 214 can be implemented in many different ways to achieve its function of creating a desired and dynamic SOBP.

For example, the wedges 502 and 504 may be made of the same material or combination of materials, or the wedges may be made of different materials or combinations of material; that is, one wedge may be made of one material or combination of materials, and another wedge may be made of a different material or materials. The materials may have different densities. Accordingly, the range shifter 214 may be made with components that are other than wedge-shaped. For example, the components may be block-shaped. The density of each block may be non-uniform such that an incident beam will pass through different densities of material depending on where and how the blocks are placed in the path of the beam and where and how the blocks are placed relative to one another. Also, different densities and thicknesses of material can be used; for example, wedge-shaped components that also have non-uniform densities can be used. The range shifter 214 can be implemented using more than two components (e.g., more than two wedges or blocks).

As mentioned above, in an embodiment, an isochronous cyclotron capable of continuous wave output can be used to generate a particle beam. In an embodiment, movement (e.g., rotational, radial, lateral) of the range modulator 212 can be synchronized with the beam source or generator (e.g., with the isochronous cyclotron). For example, sensors can be used to monitor the speed, position, and phase of the range modulator 212 and that information can be used (e.g., by the control system 110) to synchronize the movement of the range modulator to compensate for variations in the intensity of the beam output by the isochronous cyclotron or to compensate for effects of the X-Y scanning magnets 204 and 206. Then, the range shifter 214 is used to "trim" the distal edge of the planning target volume, thus reducing scatter.

Figure 6:
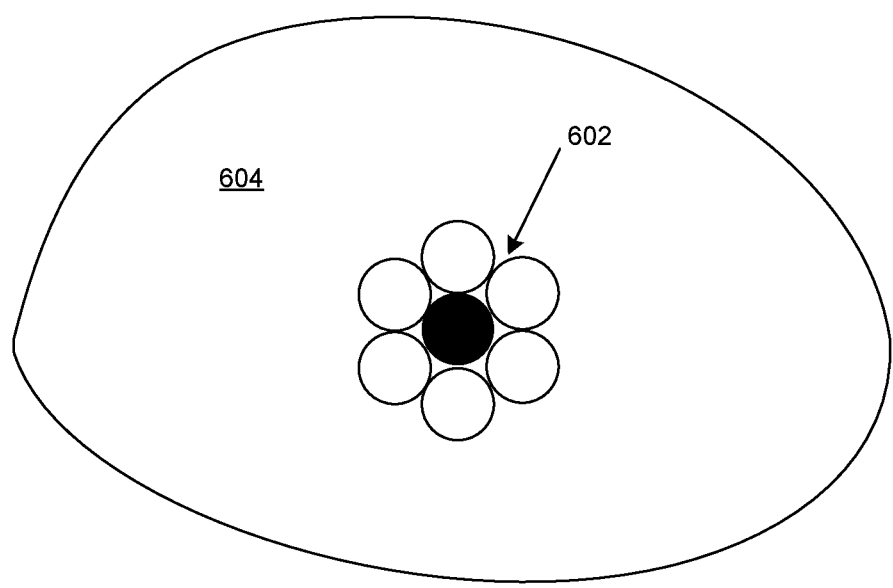
FIG. 6 illustrates a number of spots that represent the intersection of an incident particle beam with a layer of a planning target volume in an embodiment according to the present disclosure.

FIG. 6 illustrates a number of spots 602 that represent the intersection of an incident particle beam with a layer 604 of a target volume in an embodiment according to the present disclosure. In an embodiment, a variable spot size feature is incorporated by varying the current (and therefore the field strength) in focusing magnets, such as sets of quadrupole magnets located along the beam paths in the accelerator and beam transport system 104 (FIG. 1). By varying the spot size, the volume of a cylinder of targeted tissue that is exposed to radiation along a target line segment can be varied, with a corresponding inverse change in the dose rate for a given beam current. Such a capability is useful in improving the coverage and speed of dose delivery to a variety of target volume sizes and shapes. For example, a larger spot size could be useful in painting a dose over larger areas, particularly if the desired dose is not too high, while a smaller spot size may be useful in contouring a complex shape. A scan pattern can utilize staggered spots that are arranged similar to a hexagonal grid as shown in FIG. 6. The particle scatter normally encountered in a SOBP will naturally provide a penumbra region surrounding the cylinder around each target line segment. This unavoidable penumbra is useful in maintaining dose uniformity to target tissues that lie between shots. A planned extent of overlap between adjacent shots can be used to assure adequate target coverage in the "gaps" between adjacent spots of the hexagonal grid. Alternatively, a pattern of larger spots can be interleaved together with smaller spots to fill in any gaps. The extent of particle scatter and therefore the cross-sectional diameter of significant radiation dose coverage greatly increases in the region of the SOBP (e.g., within the target volume) in comparison to the region along the proximal beam (passing through healthy, normal tissue). Therefore, a significant degree of overlap of dose within the target volume from adjacent shots can be accommodated without creating a dose overlap in the normal tissue that the beam passes through. Accordingly, the positive radiobiological effects attributable to the use of shots as described herein can be preserved.

Figure 7:
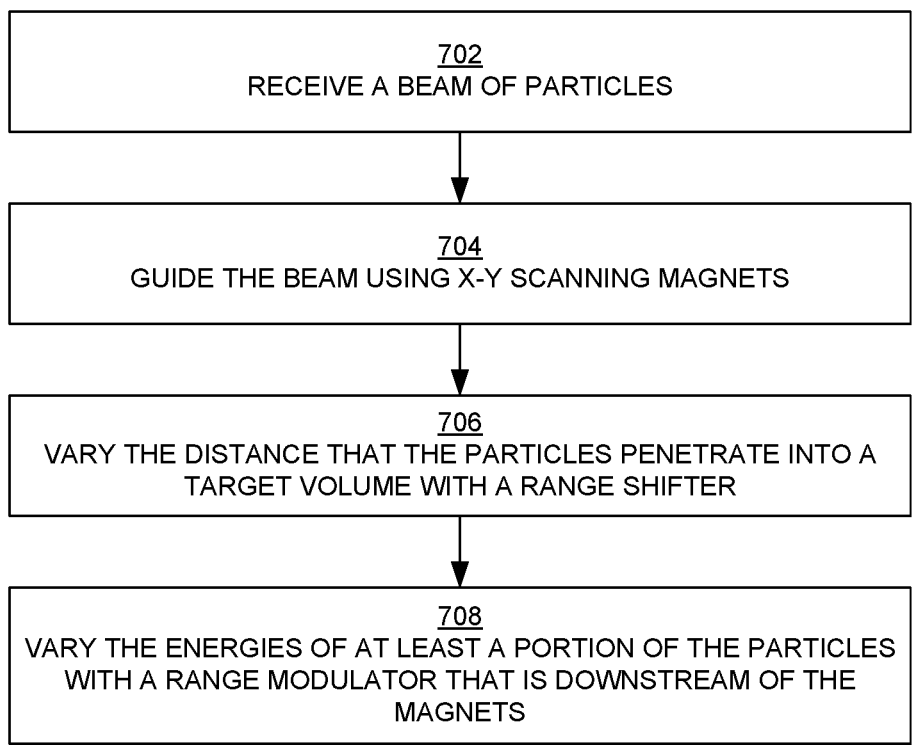
FIG. 7 is a flowchart of a radiation therapy method in an embodiment according to the present disclosure.

FIG. 7 is a flowchart 700 of a radiation therapy method in an embodiment according to the present disclosure. Although steps and sequencing thereof are disclosed in FIG. 7 describing the operations of this method, such steps and sequencing are examples. Embodiments are well suited to performing various other steps or variations of the steps recited in the flowchart 700, and in a sequence other than that depicted and described herein.

In block 702, a beam of particles is received into a nozzle.

In block 704, the beam is scanned (raster scanned) using a number of X-Y scanning magnets.

In block 706, in an embodiment, the distance that the particles penetrate into a target volume is adjusted with a range shifter that is configured to place different thicknesses of material in the path of the beam. In an embodiment, the range shifter is in the nozzle, downstream of the scanning magnets and can act as a range modulator; in another embodiment, the range shifter is in the nozzle, upstream of the scanning magnets.

In block 708, in an embodiment, the energies of at least a portion of the particles in the beam are also adjusted with a range modulator that is in the nozzle and downstream of the scanning magnets (thus the range modulator is exposed to a scanned beam).

Thus, the nozzle can be used to create an adjusted beam that delivers a dose with a SOBP along a target line segment (a shot) in a target volume aligned with the nozzle. The intensity of the dose delivered in a shot can be adjusted to match the prescribed dose for a particular target line segment. Shots can be delivered using, for example, a predefined scanning pattern to irradiate different target line segments; a first adjusted beam that delivers a first dose with a SOBP along a first target line segment in a target volume can be created, and a second adjusted beam that delivers a second dose with a second SOBP along a second target line segment in the target volume can be created, where the second target line segment is displaced from the first target line segment.

The range shifter and/or range modulator placed in the nozzle as described in this disclosure are dynamically variable (e.g., faster acting than the dipole bending magnets in the beam transport system). In an embodiment, the dose delivered along the target line segment is at least four grays and is delivered in less than one second. In another embodiment, the dose delivered along the target line segment is at least 20 grays and is delivered in less than 500 milliseconds.

In an embodiment, treatment planning and dose delivery are performed using multiple beams from different directions and nozzles, instead of using a single nozzle as described above. Each beam can be delivered at a separate time with obtuse or large acute angles between each direction. Because of the fundamental property of a particle beam in which no dose is delivered distally to the Bragg peak, no normal, healthy tissue along a ray beyond that point will receive an unwanted dose. Also, the proximal portions of any rays aimed from different beam directions do not overlap each other for directions that have an obtuse angle relative to each other. Even for beam directions at large acute angles, the extent of overlap is small. Any such overlap outside the target would reduce the positive effects attributable to the use of shots as described herein, so it is desirable to minimize any overlap.

Multiple beam directions are beneficial for at least two reasons. First, scanning dose through the target from multiple directions will greatly reduce the extent and magnitude of any dose inhomogeneity caused by the scan pattern or motion-induced range uncertainty from any one direction, as any of these effects (if present) would be overlapped within the target volume from separate directions. Second, scanning from multiple directions provides significantly greater independent degrees of freedom that can be utilized in treatment plan optimization while also significantly reducing the dose level to any normal, healthy tissue; the entrance dose is spread out over a larger volume of normal tissue.

Two nozzles, each as described above, can be placed coaxially and opposite each other with both aimed at the isocenter. A fast "kicker" magnet in a fixed beam would direct the beam back-and-forth between separate gantry-mounted paths feeding each nozzle. Scanning within each nozzle would be such that beams from both nozzles would both strike the same tissue sequentially or otherwise as close to each other in time as practical (e.g., within one second or within 500 milliseconds of each other), thus taking advantage of the positive radiobiological effects attributable to the use of shots as described herein. Because the planning target volume is typically not at the precise center of the patient, a range shifter such as the range shifter 214 described above can be employed in each nozzle to bring the SOBP from both nozzles into spatial coincidence. Because a very similar SOBP is delivered to the same target line segment from both directions, the magnitude of dose delivered to any normal, healthy tissue along the same line (proximal to the target from each direction) is reduced by half. Another advantage is that this arrangement of nozzles allows a treatment planner to independently optimize the shape and intensity of the scan pattern delivered from each direction to beneficially trade off different dose objectives or constraints during planning. For example, paired nozzles can be used to limit the dose to a specific organ-at-risk that is partially overlapping the planning target volume. No dose is delivered distally to the target beyond the Bragg peak, and this characteristic can be taken advantage of during treatment planning, especially when proton beams are to be used.

Fixed beams can also be employed rather than gantry-mounted beams, either singly or as an opposed pair as described above. The inability to preferentially aim the beam in an ideal direction is offset by a significantly lower capital expenditure. Some disease sites may not require a rotating gantry in order to be effectively treated with IMPT. For example, a pair of fixed nozzles placed in a vertical plane can be arranged to simultaneously deliver an AP/PA (anteroposterior/posteranterior) pair of opposing beams to treat a lung tumor. Similarly, a bilateral beam arrangement with opposing nozzles in a horizontal plane may be useful for other disease sites such as sites in the head and neck.

Other relative beam orientations in a multiple nozzle system (such as orthogonal) could be used, or additional nozzle beam lines and nozzles could be added (e.g., to implement three or four beam directions simultaneously).

In summary, embodiments according to the present disclosure provide spatially and temporally precise, modulated irradiation of a moving target in a patient and take advantage of the tissue-sparing effects of the study mentioned above. Embodiments according to the present disclosure provide a more direct method for target volume scanning than the use of the conventional raster scanning technique described above. Each shot is aimed directly to coincide with the in-plane motion of the target using the X-Y scanning magnets, rather than having to distort the raster scan pattern. Quality assurance is also made easier because the tracking and scanning processes are more independent of one another. Significantly, because a SOBP covering the entire length of each target line segment (from the distal edge to the proximal edge of the planning target volume) is delivered in a short burst, motion-induced uncertainties do not create gaps or overlaps (cold spots or hot spots) within the target volume.

Embodiments according to the present invention can be used to with types of external beam radiotherapy other than IMPT such as, for example, intensity modulated radiation therapy (IMRT), image-guided radiotherapy (IGRT), RapidArc™ radiotherapy, stereotactic body radiotherapy (SBRT), and stereotactic ablative radiotherapy (SABR). Embodiments according to the present disclosure can be incorporated into methods and systems used for planning radiotherapy treatments based on IMPT and other types of radiotherapy. A shot—a high dose that can be delivered in a short period of time along a target line segment—can be adjusted in energy (intensity) or range and delivered to the target volume with a SOBP that provides a uniform and otherwise suitably modified dose to an entire target line segment. The intensity of the dose delivered in a shot can be adjusted to match the prescribed dose for a particular target line segment. Subsequent shots can be independently adjusted in intensity, in range, and with a suitable SOBP, and can also be triggered or aimed to coincide with the 4D (three dimensions plus time) position of each target line segment in the scan pattern until the entire target volume has been irradiated to the prescribed dose. Radiotherapy treatments can be improved by taking advantage of this capability to quickly and accurately vary energy and range on the fly (dynamically). Treatment planning can also be improved because planners are presented with the capability to precisely control dose delivery.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A radiation therapy system, comprising:
   an accelerator and beam transport system that generates a beam of particles; and a nozzle operable for aiming the beam toward a target volume in an object and for delivering a dose along a target line segment in the target volume that is at least four grays and is delivered in less than one second.

2. The radiation therapy system of claim 1, wherein the nozzle comprises a beam energy adjuster configured to adjust the beam by affecting energies of the particles in the beam, by placing different thicknesses of material in the path of the beam in the nozzle to affect energies of particles in the beam that delivers the dose along the target line segment in the target volume.

3. The radiation therapy system of claim 2, wherein the beam energy adjuster comprises a range modulator, and wherein the range modulator is moveable in a first direction between a position that is completely out of the path of the beam and a position in the nozzle that is in the path of the beam.

4. The radiation therapy system of claim 3, wherein the range modulator is also moveable in a second direction different from the first direction and transverse to the path of the beam.

5. The radiation therapy system of claim 3, wherein movement of the range modulator is synchronized with a source of the beam to compensate for variations in the beam of particles.

6. The radiation therapy system of claim 2, wherein the beam energy adjuster comprises a range shifter configured to vary the distance that the particles penetrate into a target volume, by placing the different thicknesses of the material in the path of the beam.

7. The radiation therapy system of claim 6, wherein the range shifter comprises a plurality of components that are selectively moveable in and out of the path of the beam to present the different thicknesses of the material to the beam.

8. A radiation therapy system, comprising:
a nozzle operable for delivering a beam of particles toward a target volume; and
a control system coupled to the nozzle and operable for controlling the nozzle to aim the beam;
wherein the nozzle delivers doses along respective target line segments in the target volume in periods of time that are each short enough to coincide with each of the positions of the target volume.

9. The radiation therapy system of claim 8, wherein each of the doses delivered along the target line segment is at least four grays and is delivered in less than one second.

10. The radiation therapy system of claim 8, further comprising an accelerator and beam transport system coupled to the nozzle and that generates the beam of particles, wherein the accelerator and beam transport system comprises focusing magnets along the path of the beam.

11. The radiation therapy system of claim 8, wherein the nozzle comprises a range modulator, and wherein the range modulator is moveable in a first direction between a position that is completely out of the path of the beam and a position in the nozzle that is in the path of the beam.

12. The radiation therapy system of claim 11, wherein the range modulator is also moveable in a second direction different from the first direction and transverse to the path of the beam.

13. The radiation therapy system of claim 11, wherein movement of the range modulator is synchronized with a source of the beam to compensate for variations in the beam.

14. The radiation therapy system of claim 8, wherein the nozzle comprises a range shifter configured to vary the distance that the particles penetrate into a target volume, by placing the different thicknesses of the material in the path of the beam.

15. The radiation therapy system of claim 14, wherein the range shifter comprises a plurality of components that are selectively moveable in and out of the path of the beam to present the different thicknesses of the material to the beam.

16. A radiation therapy system, comprising:
an accelerator and beam transport system that generates a beam of particles, wherein the accelerator and beam transport system comprises focusing magnets along the path of the beam; and
a nozzle operable for aiming the beam toward an object, wherein the nozzle comprises:
scanning magnets operable for steering the beam toward different locations within the object; and
a beam energy adjuster configured to adjust the beam by affecting energies of the particles in the beam, wherein the beam energy adjuster comprises a range modulator configured to place different thicknesses of material in the path of the beam to change the energies of at least a portion of the particles and achieve a Spread Out Bragg Peak along a target line segment in a target volume, wherein the dose delivered along the target line segment is delivered in less than one second.

17. The radiation therapy system of claim 16, wherein the beam energy adjuster comprises a range modulator, and wherein the range modulator is moveable between a position that is completely out of the path of the beam and a position in the nozzle that is in the path of the beam.

18. The radiation therapy system of claim 16, wherein the beam energy adjuster comprises a range shifter configured to vary the distance that the particles penetrate into a target volume, by placing the different thicknesses of the material in the path of the beam.

* * * * *